(12) United States Patent
Zeppezauer et al.

(10) Patent No.: US 7,902,146 B2
(45) Date of Patent: Mar. 8, 2011

(54) THERAPEUTIC, PROPHYLACTIC, AND DIAGNOSTIC AGENT FOR CANCER, USEFUL FOR CHARACTERIZING CANCER CELLS WITH INDIVIDUAL PROPERTIES

(76) Inventors: Michael Zeppezauer, Scheidt (DE); Hans-Peter Leinenbach, Tholey (DE); Reiner Class, Drexel Hill, PA (US); Cordula Fassbender, Cologne (DE)

( * ) Notice: Subject to any disclaimer, the term of this patent is extended or adjusted under 35 U.S.C. 154(b) by 359 days.

(21) Appl. No.: 11/656,009

(22) Filed: Jan. 22, 2007

(65) Prior Publication Data

US 2007/0203067 A1    Aug. 30, 2007

Related U.S. Application Data

(63) Continuation of application No. 10/238,726, filed on Sep. 11, 2002, now abandoned, which is a continuation of application No. 09/402,468, filed as application No. PCT/EP98/02112 on Apr. 9, 1998, now abandoned.

(51) Int. Cl.
*A01N 37/18*    (2006.01)

(52) U.S. Cl. ............................................. 514/2; 435/7.23

(58) Field of Classification Search ..................... None
See application file for complete search history.

(56) References Cited

U.S. PATENT DOCUMENTS

| | | | |
|---|---|---|---|
| 4,818,763 A | 4/1989 | Rusch et al. | |
| 5,182,257 A * | 1/1993 | Zeppezauer et al. | 514/2 |
| 5,744,335 A * | 4/1998 | Wolff et al. | 435/458 |
| 6,074,835 A | 6/2000 | Braun et al. | |

FOREIGN PATENT DOCUMENTS

| | | |
|---|---|---|
| DE | 3737274 A | 6/1989 |
| EP | 0392315 A | 10/1990 |
| EP | 0438756 A | 7/1991 |
| WO | 9321943 A | 11/1993 |

OTHER PUBLICATIONS

Class et al, Am J Clin Oncol, Oct. 1996, 19:522-531.*
R. Class et al., Histone H1 Suppresses Tumor Growth of Leukemia Cells in Vitro, Ex Vivo and in Animal Model Suggesting Extracellular Functions of Histones, American Journal of Clinical Oncology (Cancer Clinical Trials), Oct. 5, 1996, XP002073894.
Wells et al., Nucleic Acids Research, vol. 17, Supplement, 1989, pp. 311-346.
Parseghian et al., Chromosome Research, vol. 1(2), 1993, pp. 127-139.
Briand et al., FEBS Letters, vol. 112(2), 1980, pp. 147-151.
Turner, BM, Bioassays, vol. 17(12), 1995, pp. 1013-1015.
Kamei et al., Biotherapy, 1992, vol. 4(1), abstract only.
Bosch et al., Eur. J. Cancer, 1993, vol. 29A(10), abstract only.

* cited by examiner

*Primary Examiner* — Misook Yu
*Assistant Examiner* — Mark Halvorson
(74) *Attorney, Agent, or Firm* — Bacon & Thomas PLLC

(57) ABSTRACT

A therapeutic or prophylactic agent for cancer is disclosed which damages the membrane and kills cancer cells, in particular of the blood-forming system, having membrane protein aggregates which contain several core histones or largely core-like histones and/or their parts. The therapeutic or prophylactic agent contains at least one pure histone or its active sequence section selected from the group composed of histone H1, H1 subtypes, H2A, H2B, H2A:H2B dimer, H3 and H4, covalent modified histones of the above-mentioned type and/or their active sections and functionally and structurally similar proteins (protamines, histone-like proteins of prokaryotic and archae bacteria).

7 Claims, 5 Drawing Sheets

A

B

C

D

Figure 1:
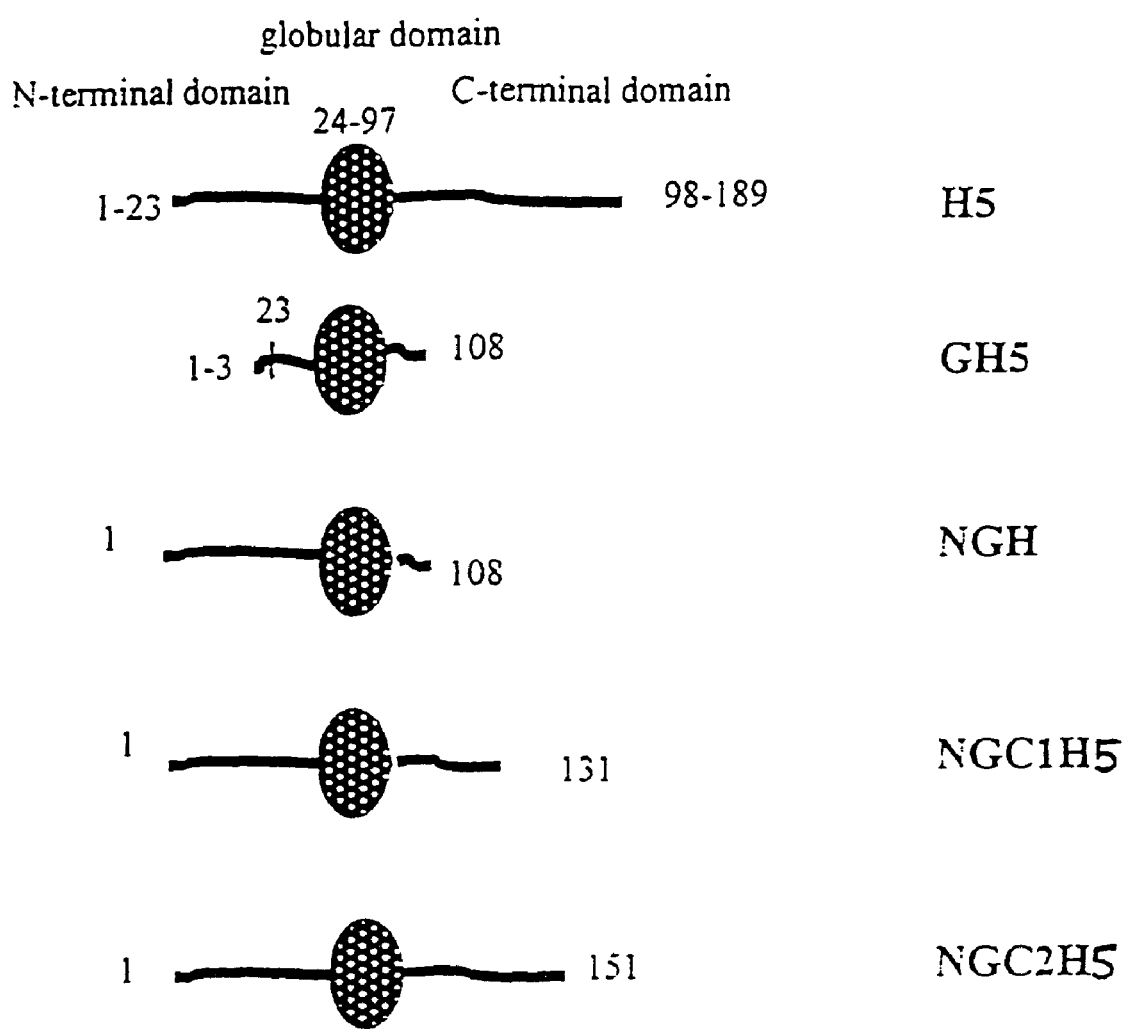

THERAPEUTIC, PROPHYLACTIC, AND DIAGNOSTIC AGENT FOR CANCER, USEFUL FOR CHARACTERIZING CANCER CELLS WITH INDIVIDUAL PROPERTIES

This application is a continuation application of pending U.S. application Ser. No. 10/238,726, filed Sep. 11, 2002 now abandoned (of which the entire disclosure of the pending prior application is hereby incorporated by reference), which is a continuation application of pending U.S. application Ser. No. 09/402,468, filed Oct. 12, 1999 now abandoned (of which the entire disclosure of the pending, prior application is hereby incorporated by reference), which is the national stage of PCT/EP98/02112, filed Apr. 9, 1998.

The invention relates to histones and/or histone-like proteins (i.e. protamines, bacterial histone-like proteins) as a therapeutic and prophylactic agent against cancer cells and is a continuation of application Ser. No. 09/402,468, the entire disclosure of which is herein incorporated by reference.

According to Reiner Class et al. (in American Journal of Clinical Oncology (CCT) 19 (5) 1996, pp. 552-531), the effect of histones on cancer cells is due to the fact that those cancer cells, which are killed by histone H1, express a so called receptor protein in their membranes that is able to bind histone H1. Said receptor protein has been isolated by affinity chromatography using immobilized histone H1. It has been determined by sodium dodecyl sulfate polyacrylamide gel electrophoresis (SDS-PAGE) that the receptor protein has an electrophoretic mobility corresponding to a molecular mass of approximately 33,000 Da (33 k Da) ±2,000 Da.

The binding of histone H1 to the membrane-embedded receptor protein causes a destruction of the membrane integrity, resulting in an uncontrolled efflux of soluble cellular components such as proteins, ions and other molecules and influx of other substances, ultimately resulting in cell death.

The invention is based on the rationale that tumor cells of different histological origin (e.g. leukemia, lymphomas, sarcomas, carcinomas, melanomas etc.) possess special individual properties and that a better understanding of said individual and cell line-specific properties can offer a starting point for a novel and effective therapy. It could be demonstrated that the receptor protein is not characteristic for a single or several distinct cell types but rather represents an individual, cell line-characteristic property that can be made accessible for a targeted therapy.

The invention has set its ultimate goal to obtain more knowledge about the receptor protein, translating into a novel teaching for therapeutic and prophylactic treatments or suppressions of individual cancer cells expressing such receptor proteins.

Therefore, the invention also comprises a diagnostic tool for the recognition of those cancer cells that express (as an individual characteristic) such receptor proteins, which makes the success of the teaching for the therapeutic treatment of said individual cancer cells (i.e. the outcome) predictable. This implies that cancer cells can be classified in a novel way depending on the success of the treatment with the therapeutic agent (i.e. histone H1). As soon as reliable data become available that can predict the predisposition of distinct people to develop cancer cells with said individual properties, the therapeutic (that is subject of this invention) can also be used in a prophylactic regimen. This will be especially applicable if the natural level of histones in the blood of these people has been recognized as too low.

This invention is founded on the observation that above receptor protein in the membrane of individual cancer cells (especially cancer cells of the hematopoietic system such as leukemias, lymphomas and myelomas) contains several histone proteins or histone-like polypeptides and/or parts thereof or is largely composed of them. These proteins can bind and cross link with externally added histones or histone-like proteins (e.g. protamine and bacterial histone-like proteins), whereby the regimen can be of therapeutic or diagnostic nature. Appropriate antibodies that recognize the receptor proteins can also be utilized as diagnostic tools.

Advantageous executions result from the characteristics of the claims and from the following description.

Figure 2:
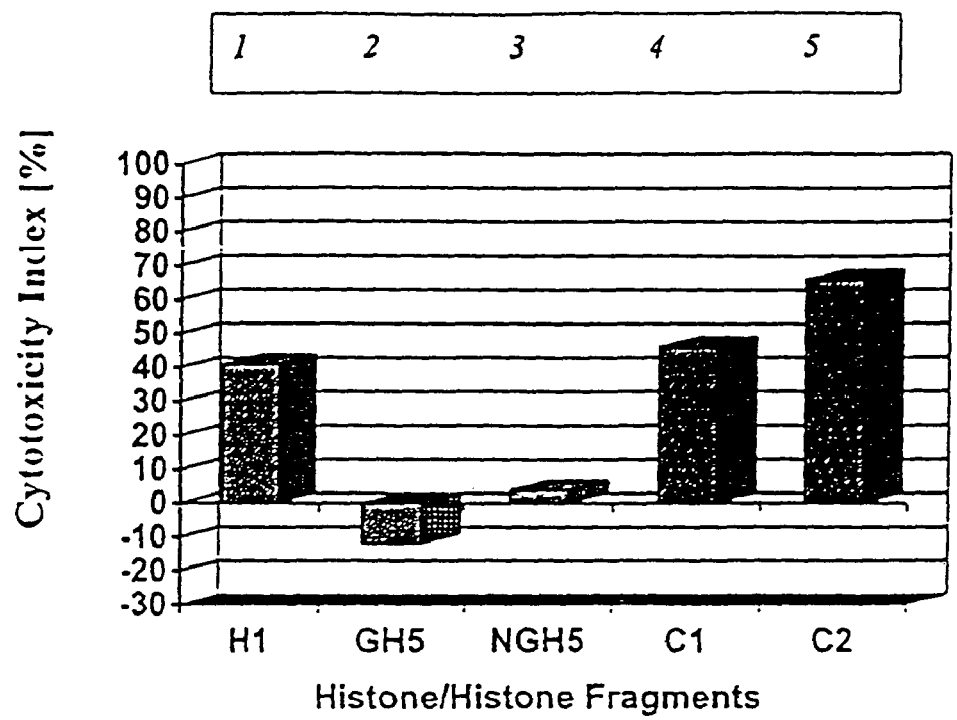
Figure 3:
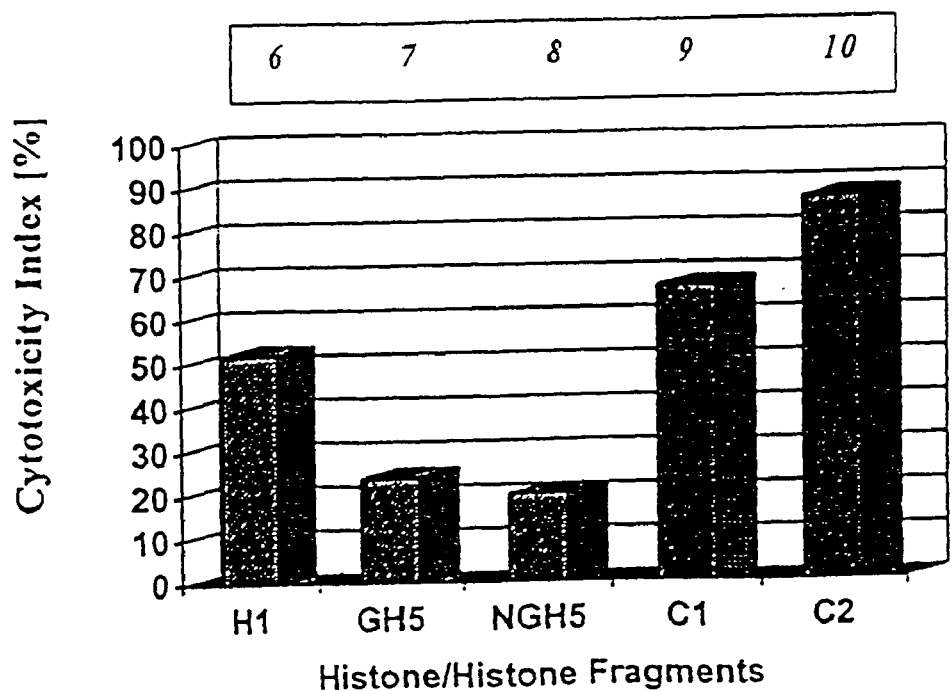
Figure 4:
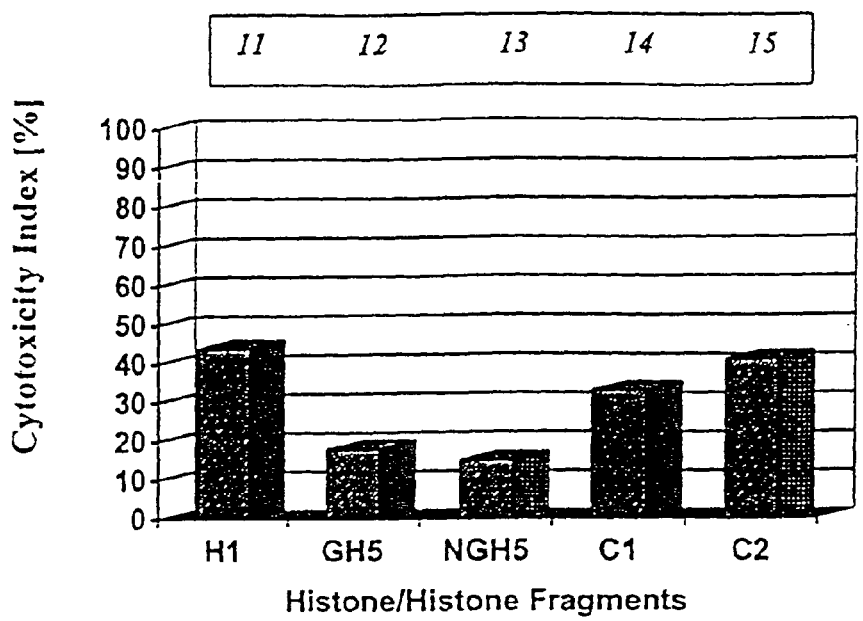
Figure 5:
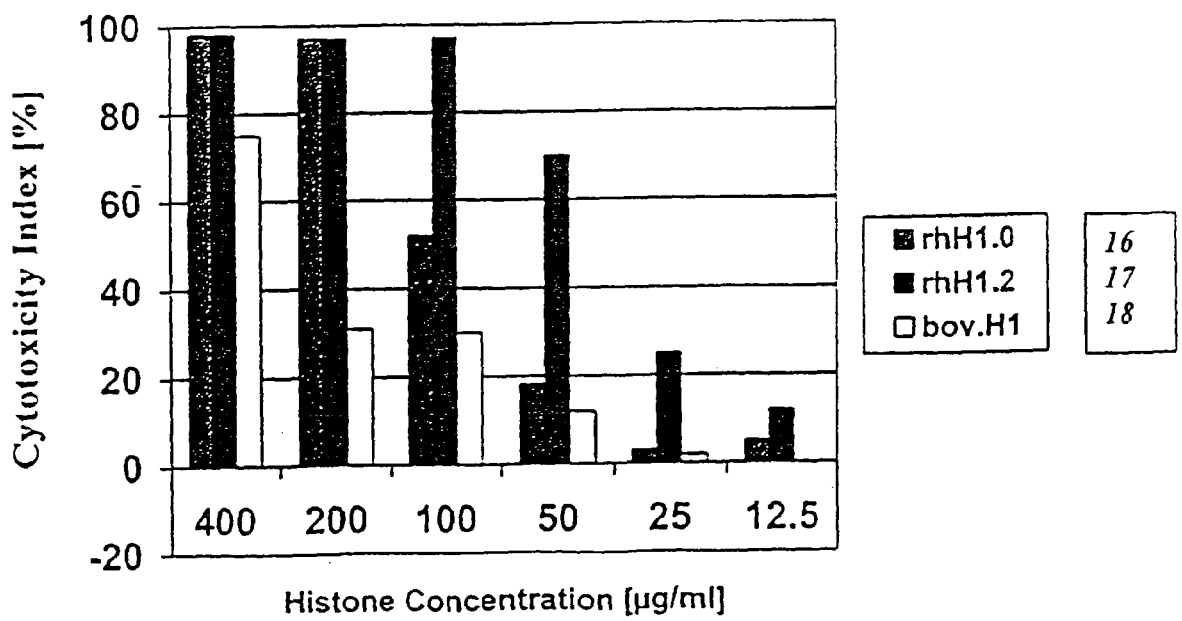
Figure 6:
Figure 6:
Figure 7:
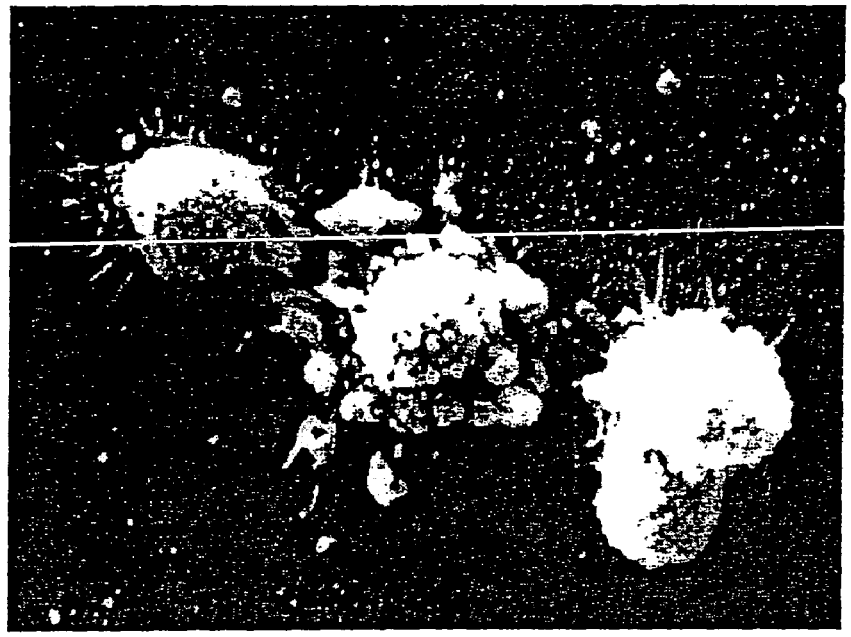
Figure 7:

In the description, the figures show respectively:

FIG. 1 Recombinantly produced fragments of histone H5;

FIG. 2 examples 1 to 5, regarding the cytotoxicity of histone H1 and recombinant histone fragments towards acute myeloid leukemia;

FIG. 3 examples 6 to 10, regarding the cytotoxicity of histone H1 and recombinant histone fragments towards cell line IM9;

FIG. 4 examples 11 to 15, regarding the cytotoxicity of histone H1 and recombinant histone fragments towards cell line OH77;

FIG. 5 examples 16 to 18, regarding the cytotoxicity of histone H1 and recombinant histone fragments towards cell line Daudi;

FIG. 6 photographs A and B of untreated cells of cell line OH77 at different magnifications; and FIG. 7 photographs C and D tumor cells treated with histone H1.

Histone-like proteins are defined here as protamines and distinct bacterial proteins. Some of the histone-like proteins of bacterial origin are listed in table 1 including relevant references from the literature. The similarity between the listed bacterial histone-like proteins with histones has been determined from a structural point of view by X-ray crystallography on protein crystals, from a functional point of view by DNA-binding and transcription studies, and from a biochemical point of view by sequence homologies with histone H1.

TABLE 1

| Protein | BaCteria | Reference |
|---|---|---|
| HMf<br>HAN1<br>HAN2 | *Methanothermus*<br>*fervidus* | Ronimus, R. S. and Musgrave, D. R.(1996)<br>Purification and characterization of a histon-like protein from<br>Archaeal isolate AN1, a member of the Thermococcales.<br>Mol. Microbiol., 20: 77-86 |
| HAN1 | *Thermococcus*<br>spec. | Ronimus, R. S. and Musgrave. D. R. (1996)<br>A gene, han1A, encoding an archaeal histone-like protein<br>from the *Thermococcus* species AN1: homology with<br>eukaryal histone consensus sequences and the implications for<br>delineation of the histone fold.<br>Biochim.Biophys.Acta, 1307: 1-7 |
| HMfA | *Methanothermus* | Decanniere, K., Sandman, K., Reeve, J. N., Heinemann, U. |

TABLE 1-continued

| Protein | BaCteria | Reference |
|---|---|---|
| HMfB | fervidus | (1996)<br>Crystallization and preliminary X-ray characterization of the *Methanothermus fervidus* histones MMfA and HMfB.<br>Proteins, 24: 268-71 |
| Hc1<br>Hc2 | Chalmydia<br>trachomatis | Petersen, L. B., Birkelund, S., and Christiansen, G. (1996)<br>Purification of recombinant *Chlamydia trachomatis* histone H1-like protein Hc2, and comparative functional analysis of Hc2 and Hc1.<br>Mol. Microbiol., 20: 295-311 |
| MC1 | Methanosarcina spec. | Teyssier, C., Toulme, F., Touzel, J. P., Gervais, A., Maurizot, J. C., and Culard, F. (1996)<br>Preferential binding of the archaebacterial histone-like MC1 protein to negatively supercoiled DNA minicircles.<br>Biochemistry, 35: 7954-7958 |
| BpH1 | Bordetella pertussis | Scarlato, V., Arico, B., Goyard, S., Ricci, S., Manetti, R., Prugnola, A., Manetti, R., Polverino-De-Laureto, P., Ullmann, A., and Rappuoli, R. (1995)<br>Mol. Microbiol., 15: 871-881 |

Initially, the above mentioned receptor protein in the membrane of individual cancer cells has been characterized by the inventors.

The mass spectrometric analysis of the protein bands derived from SDS-PAGE using MALDI-MS technique (matrix-assisted laser desorption/ionization mass spectrometry) revealed that the electrophoretically homogeneous band contained three different proteins with the molecular masses of 11.2, 13.7, and 15.0 kDa.

In detail, the following mean values have been obtained:
11,175±40 kDa
13,730±40 kDa and
15,035±80 kDa The mean values are calculated from single- and double charged molecule ion signals and from 4 to 6 sum-spectra, acquired from the examined samples.

In comparison to above molecular masses of the receptor polypeptides, the below listed human histone sequences have the following molecular masses:
H4 11,282 kDa
H2B 13,774 kDa
H3 15,324 kDa and
H2 14,004 kDa The sequence analysis by automated Edman protein degradation identified a peptide sequence that corresponded to amino acid residues 23 to 59 of human histone H4, differing only in position 23 and 35. This represents a 97.2% homology compared to the known sequence of histone H4 in healthy cells.

These findings justify the surprising conclusion that the mentioned receptor protein consists of or contains those proteins that can be related to the histones H4, H2B, and H3 or to proteins very similar to them. The presence of histone proteins in the membrane of individual cancer cells is most likely due to the tumorigenic transformation which these cells undergo, likewise their quantitative composition and potential structural differences compared to the nuclear histones.

According to the invention, the histone proteins belonging to the histones H2A, H2B, H3 and/or H4 (the so called core histones) that are expressed in the cell membrane of individual cancer cells at comparatively high concentrations can be cross-linked by the external addition of histones, especially histone H1 or of active components thereof. The cross-linking causes a loss of membrane integrity in the particular cancer cell, ultimately resulting in cell death. Mentioned histone proteins can be of natural origin, e.g. extracted from bovine tissue, or can be recombinant proteins. Covalently modified histone proteins or parts thereof or functionally and structurally similar proteins can also be used. Suitable covalent modifications include but are not restricted to derivatization with polyoxyethylene chains ("pegylation"). An example for functionally and structurally similar proteins is protamines or histone-like proteins from prokaryotic organisms or archebacteria.

It is a known that histone H1 molecules serve as linker between the so-called nucleosomes, a well-organized complex of core histones, thus forming the condensed structure of the chromatin. To achieve this, largely intact histone H1 molecules are required, containing a compact and folded central part (i.e. the globular domain) with the adjacent flexible N— and C-terminal domains.

One could deduct from this knowledge a method to pinpoint the biologically active (i.e. cytotoxic) domains of the histone H1 molecule that still guarantees the cross-linking with or binding to those core histones that are expressed in cell membranes of individual cancer cells.

For this, recombinantly manufactured histone H5 has been used partly in cytotoxicity experiments. Histone H5 is derived from chicken erythrocytes and represents the erythrocyte-specific variant of histone H1. Fragments of this histone protein have been employed partly in which either both terminal tails have been extensively shortened or in which the C-terminal tail has been gradually shortened. These fragments and their manufacturing by genetechnology methods have been described by Gerchman et al. in Protein Expression & Purification, 5(1994), pages 242-251.

FIG. 1 shows the employed H5-fragments and their structural composition. They are: the whole histone H5 molecule (H5), essentially the globular domain only (GH5), the globular domain with the N-terminal domain (NGH5), the globular domain with the N-terminal domain and the C-terminal amino acids 98-131 (NGC1H5), and finally, the globular domain with the N-terminus and the C-terminal amino acids 98-151 (NGC2H5). All proteins and culture media used have been tested negative for endotoxin.

FIG. 1 as a graphic representation of the three structural domains of the histone molecules H5 (GH5, NGH5, NGC1H5, and NGC2H5) describes recombinantly produced histone fragments.

To investigate potential structure-function relationships of the effect of calf thymus-derived histone H1 on transformed cancer cells, a series of experiments has been performed, comparing histone H1 with above listed recombinant polypeptide fragments of histone H5. The following cells/cell lines have been tested: a primary cell line derived from the peripheral blood of a female patient with acute myeloid leukemia (AML), cells of the leukemia cell line IM9, and cells of the lymphoma cell line OH77. In all experiments, histone H1 was cytotoxic at a concentration of 250 ig/ml. The cytotoxic effects of the longer recombinant H5-derived polypeptides, NGC1H5 and NGC2H5, towards cells of the AML and the lymphoma cell line were comparable to histone H1 whereas stronger cytotoxic effects could be observed for the cell line IM9. The smallest growth inhibitory effects have been induced in all cell types by the globular domain GH5 and the fragment NGH5. The recombinant fragments have been used in concentrations equimolar to 250 ig/ml histone H1. The results are summarized in the following examples 1-5.

FIG. 2 shows the cytotoxicity of histone H1 and the recombinant histone fragments towards leukemia cells of a female patient with AML (acute myeloid leukemia). In examples 1 to 5, $1 \times 10^6$ cells/ml have been incubated for 48 h under the following standard conditions:

H1: Histone H1; recombinant fragments of histone H5: GH5: fragment GH5; NGH5: fragment NGH5; C1: fragment NGC1H5; C2: fragment NGC2H5. Histone H1 and the recombinant fragments have been employed at 12 iM. The viability of the cells has been determined using the MTT method. Shown are the mean values of 4 parallel experiments.

In FIG. 3 and in examples 6 to 10, the cytotoxic effects of histone H1 and recombinant histone fragments are shown for cells of the myeloid leukemia cell line IM9.

Furthermore, in FIG. 4 and examples 11 to 15 show the cytotoxic effects of histone H1 and recombinant histone fragments for cells of the lymphoma cell line OH77.

In examples 6 to 15, $5 \times 10^4$ cells/ml have been incubated for 48 h under the following standard conditions:

H1: Histone H1; recombinant fragments of histone H5: GH5: fragment GH5; NGH5: fragment NGH5; C1: fragment NGC1H5; C2: fragment NGC2H5. Histone H1 and all recombinant H5 fragments have been incubated at 12 iM. The viability of the cells has been determined using the MTT method. Shown are the mean values of 4 parallel experiments.

From the examples it follows that the globular domain of the histone H1 (or H5) molecule GH5 possesses only a small or no cytotoxic effects at all (indicated by a cytotoxicity index smaller than 20). Similar is valid for the fragment NGH5. which almost completely lacks the C-terminal domain. If at least the residues 108 to 131 are present and if the N-terminal domain is intact (NGC1H5), a fragment results whose cytotoxic activity reaches or even surpasses that of intact histone molecule (see examples 4 and 9). The same is true for NGC2H5. which is lacking only 38 amino acids of the C-terminal domain.

Similar relationships count respectively for histone fragments with shortened N-terminal domain and intact C-terminal domain.

According to the invention, it suggests itself to use human histone H1 subtypes instead of histone H5, especially the subtypes H1.1, H1.2, H1.3, H1.4, and H1.0 or parts thereof.

FIG. 5 and examples 16 and 17 show the cytotoxic activity of recombinantly produced human (rh) histone H1 subtypes H1.0 and H1.2 in comparison to calf thymus-derived (bovine) histone H1 towards cells of the burkitt lymphoma cell line Daudi (FIG. 5, example 18).

The following table 2 lists the mentioned human histone H1 subtypes with their respective N- and C-terminal domains. The corresponding globular domain between the N- and C-terminal domains has not been listed here. In analogy to the results obtained with the histone H5 from chicken, it is reasonable to expect that these subtypes exert similar cytotoxic effects towards those cancer cells that contain membrane-standing core histone receptors.

TABLE 2

| N-terminal domain | C-terminal domain | Necessary N-terminal domain | Necessary C-terminal domain |
|---|---|---|---|
| H1.1 1-40 | 118-214 | from 16; 20-26 | 118-138 |
| H1.2 1-38 | 105-212 | from 16; 20-26 | 105-125 |
| H1.3 1-39 | 117-220 | from 16; 20-26 | 117-137 |
| H1.4 1-38 | 116-218 | from 16; 20-26 | 116-136 |
| H1.0 1-25 | 99-193 | from 11; 16-20 | 99-119 |

In this above listed gradation, the C- and N-terminal domains have been defined as those areas that contain the amino acid proline (P) in their sequences, because proline prohibits the formation of helices by causing a stretching of the polypeptide chain.

In the literature, the borders of the domains are defined differently. In the case of the chicken histone H5, some authors define the N-terminus as amino acids 1 to 18, and the globular domain as amino acid 19 to 108, whereas Gerchman et al. (in the preceding reference) define the globular domain as amino acids 24 to 96.

In summary, one can conclude that the proteins of the individual receptor of cancer cells—based on current knowledge—represent an aggregate of the core-histones H2A, H2B, H3 and/or H4 or that it contains such histones or core histone-like proteins. Whether DNA is present on the membrane surface cannot be determined conclusively. However, it cannot be excluded.

Additionally, it cannot be excluded that protamines can be synthesized in cancer cells as a consequence of their neoplastic transformation. These protamines can then be localized in the cell membrane instead of the core histones or together with the core histones, forming complexes with and binding to histones or histone-like proteins.

Histones belonging to the nucleosome (i.e. core histones) are connected to each other tightly by non-covalent forces thus mimicking a higher molecular weight. They are also associated with each other in the cell membrane where they end up due to a transformation-dependent disturbance in the regulation.

The mechanism of action of the therapeutic agent, which is subject of this invention, is based-on the cross linking of membrane-standing histone proteins through (a) externally administered histone proteins, especially histone H1 and parts thereof that can be cross linked, (b) biologically active, covalently modified histones or (c) through functionally and/or structurally histone-like proteins. As a consequence of this cross-linking or binding, larger aggregates are formed within the cell membrane. These aggregates have a pore-like character, give raise to the formation of pores or cause mechanical deformation of cell membrane components that are directly associated with structural components of the cytoskeleton. These events result in the disruption of the cell membrane integrity and, ultimately, cell death. It is possible that signal transduction mechanisms and apoptotic processes are involved in this but they are not the determining process that leads to cell death.

The biological activity of the therapeutic agent, which is subject of this invention, is made clear in photographs A and B of FIG. 6 and photographs C and D in FIG. 7.

In FIG. 6, photograph A shows untreated cells of the lymphoma cell line OH77 (magnification 2,000-fold), photograph B is a detail from photograph A at a 20,000-fold magnification. Through this, the typical surface structure of an intact lymphatic tumor cell is clarified.

In FIG. 7, photograph D depicts the drastic change of the tumor cells after 12 hours incubation with 200 ig/ml histone H1. It becomes evident that the cells contract to a sphere-like shape and, after a 24 hours incubation time with histone H1, completely disintegrate (as shown in photograph C of FIG. 7).

The pure histone H1 preparation has been employed at the above listed concentration and was resuspended in normal media used for cell culture as described in the previously listed reference.

The invention also includes a method for the diagnosis of individual cancer cells expressing the described receptor protein in their membrane. According to the invention, those histones—especially histone H1 or active parts thereof or suitable antibodies—will be used for diagnosis that bind to the receptor protein on cancer cells thus allowing for the first time a classification of individual cancer cells containing this particular receptor protein. The diagnostic techniques needed for this are widely known and state-of-the-art. The same is valid for a technique to find suitable antibodies, which recognize the receptor protein itself in the membrane of cancer cells or related structures formed by aggregation.

We claim:

1. A method of treating cancer in a patient in need thereof, wherein the method comprises:
    (a) determining whether or not cancer cells from the patient comprise receptor proteins which consist of or comprise histones H2A, H2B, H3 and/or H4; and
    (b) if cancer cells from the patient comprise receptor proteins which consist of or comprise histones H2A, H2B, H3 and/or H4, then administering to the patient a therapeutically effective amount of a medicinal product comprising histone H1 or H5.

2. The method of claim 1, wherein the histone H1 or H5 cross-links with the histones on the cancer cells resulting in a loss of cell membrane integrity.

3. The method of claim 1, where the medicinal product comprises at least one human histone H1-subtype.

4. The method of claim 1, where the medicinal product comprises at least one recombinant histone H1-subtype.

5. The method of claim 1, wherein the cancer is leukemia.

6. The method of claim 2, wherein the cancer is leukemia.

7. The method of claim 2, wherein the medicinal product comprises histone H1.

* * * * *